(12) United States Patent
Doane et al.

(10) Patent No.: US 10,961,475 B2
(45) Date of Patent: *Mar. 30, 2021

(54) ASPHALTENE DISPERSANT COMPOSITION

(71) Applicant: SI Group, Inc., Schenectady, NY (US)

(72) Inventors: Joseph T. Doane, Rotterdam Junction, NY (US); Kelly S. Chichak, Halfmoon, NY (US); Brian Christofel, Glenville, NY (US); Elliott W. Shanklin, Altamont, NY (US)

(73) Assignee: SI Group, Inc., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,768

(22) Filed: Mar. 6, 2019

(65) Prior Publication Data

US 2019/0276660 A1 Sep. 12, 2019

Related U.S. Application Data

(60) Provisional application No. 62/799,858, filed on Feb. 1, 2019, provisional application No. 62/795,262, filed on Jan. 22, 2019, provisional application No. 62/671,850, filed on May 15, 2018, provisional application No. 62/671,800, filed on May 15, 2018, provisional application No. 62/671,728, filed on May 15, 2018, provisional application No. 62/639,037, filed on Mar. 6, 2018.

(51) Int. Cl.
| | |
|---|---|
| *C10L 1/198* | (2006.01) |
| *C10L 10/16* | (2006.01) |
| *C10L 1/195* | (2006.01) |
| *C08G 8/10* | (2006.01) |
| *C08G 8/08* | (2006.01) |
| *C08L 61/06* | (2006.01) |
| *C10G 75/02* | (2006.01) |
| *C10G 71/00* | (2006.01) |
| *C10G 75/04* | (2006.01) |
| *C07C 39/06* | (2006.01) |
| *C07C 39/15* | (2006.01) |

(52) U.S. Cl.
CPC ............ *C10L 1/1981* (2013.01); *C07C 39/06* (2013.01); *C07C 39/15* (2013.01); *C08G 8/08* (2013.01); *C08G 8/10* (2013.01); *C08L 61/06* (2013.01); *C10G 71/00* (2013.01); *C10G 75/02* (2013.01); *C10G 75/04* (2013.01); *C10L 1/195* (2013.01); *C10L 10/16* (2013.01); *C10G 2300/206* (2013.01); *C10G 2300/80* (2013.01)

(58) Field of Classification Search
CPC ........ C08L 61/06; C10L 1/1981; C07C 39/15; C07C 39/06; C10G 75/04; C10G 2300/80; C10G 2300/206; C08G 8/08; C08G 8/12
USPC ................ 585/1, 3; 568/716, 717, 718, 720; 252/71, 77
See application file for complete search history.

(56) References Cited

U.S. PATENT DOCUMENTS

| | | |
|---|---|---|
| 4,151,069 A | 4/1979 | Rossi |
| 4,514,314 A | 4/1985 | Rossi |
| 5,021,498 A | 6/1991 | Stephenson et al. |
| 5,039,437 A | 8/1991 | Martella et al. |
| 5,571,506 A | 11/1996 | Regan et al. |
| 5,851,429 A | 12/1998 | Magyar |
| 6,180,683 B1 | 1/2001 | Miller et al. |
| 7,417,009 B2 | 8/2008 | Shmakova-Lindeman |
| 2003/0171221 A1 | 9/2003 | Feustel et al. |

(Continued)

FOREIGN PATENT DOCUMENTS

| | | |
|---|---|---|
| WO | WO2005054321 | 6/2005 |
| WO | WO2017120286 | 7/2017 |

(Continued)

OTHER PUBLICATIONS

International Search Report and Written Opinion for PCT/US2019/020923, dated Jun. 17, 2019, 10 pages.

(Continued)

*Primary Examiner* — Thuan D Dang
(74) *Attorney, Agent, or Firm* — Dority & Manning, P.A.

(57) ABSTRACT

An asphaltene dispersant composition is provided. The composition may contain an alkylphenol copolymer having the following repeating units (A) and (B):

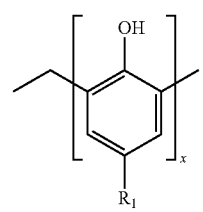

(A)

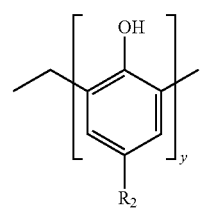

(B)

wherein,
x is an integer from 1 to 200;
y is an integer from 2 to 200;
$R_1$ is a straight or branched $C_1$-$C_{15}$ alkyl; and
$R_2$ is a straight or branched $C_2$-$C_{40}$ alkyl, wherein $R_2$ is different than $R_1$.

17 Claims, 3 Drawing Sheets

(56) References Cited

U.S. PATENT DOCUMENTS

| | | |
|---|---|---|
| 2004/0058827 A1 | 3/2004 | Jennings |
| 2004/0266973 A1 | 12/2004 | Strickland et al. |
| 2013/0150272 A1 | 6/2013 | Sonne et al. |
| 2014/0336285 A1 | 11/2014 | Cendejas Santana et al. |
| 2017/0292657 A1 | 10/2017 | Kundu |
| 2017/0355798 A1 | 12/2017 | Kundu et al. |

FOREIGN PATENT DOCUMENTS

| | | |
|---|---|---|
| WO | WO2017177009 | 10/2017 |
| WO | WO2018190917 | 10/2018 |
| WO | WO2019005680 | 1/2019 |

OTHER PUBLICATIONS

Goual et al., "Asphaltene aggregation and impact of alkylphenols," Langmuir, 2014, vol. 30, No. 19, pp. 5394-5403.

Related Applications Form.

Ghaffar et al., "Synthesis of Poly(dodecyl phenol formaldehyde)-b-poly(oxypropylene) Block Copolymer, and Evaluation as Asphaltene Inhibitor and Dispersant," Springer Link, Jan. 2015, vol. 41, Issue 1, pp. 443-455.

Venkatesan et al., "The Strength of Paraffin Gels Formed Under Static and Flow Conditions," Chemical Engineering Science 60 (2005) 3587-3598.

ASPHALTENE DISPERSANT COMPOSITION

RELATED APPLICATIONS

This application claims filing benefit of U.S. Provisional Patent Application No. 62/639,037 having a filing date of Mar. 6, 2018, U.S. Provisional Patent Application No. 62/671,728 having a filing date of May 15, 2018, U.S. Provisional Patent Application No. 62/671,800 having a filing date of May 15, 2018, U.S. Provisional Patent Application No. 62/671,850 having a filing date of May 15, 2018, U.S. Provisional Patent Application No. 62/795,262 having a filing date of Jan. 22, 2019, and U.S. Provisional Patent Application No. 62/799,858 having a filing date of Feb. 1, 2019, all of which are hereby incorporated by reference in their entirety.

BACKGROUND OF THE INVENTION

Various types of petroleum sources, such as heavy crude oils and residual fuel oils, may be rich in asphaltenes. Asphaltenes are heterocyclic unsaturated macromolecules that are primarily formed of carbon and hydrogen, but also contain other minor components, such as sulphur, oxygen, nitrogen, and various heavy metals. Due to their chemical complexity, asphaltenes are generally classified by their insolubility in n-alkane fluids, in which they are usually present as a colloidal dispersion. Under normal reservoir conditions, asphaltenes are in equilibrium in the crude oil. As crude oil is produced, however, the equilibrium may be altered by a number of factors, such as by carbon dioxide injection, pH change, pressure drop, shear, streaming potential through porous media, etc., which can ultimately result in precipitation and possibly deposition of the asphaltenes onto surfaces. Asphaltene deposition can occur at any location of a crude oil production cycle, such as in perforations, tubing, downhole and surface chokes, or surface flowlines. Regardless of where it occurs, asphaltene sludging or deposition may cause significant operational problems during production and processing of crude oils. To help minimize these problems, various asphaltene dispersants or deposition inhibitors have been employed in an attempt to inhibit the precipitation of asphaltenes and/or disperse any asphaltene precipitates formed in a petroleum source. Unfortunately, conventional asphaltene dispersants are still not completely effective.

As such, a need continues to exist for an asphaltene dispersant composition that can exhibit improved performance.

SUMMARY OF THE INVENTION

In accordance with one embodiment of the present invention, an asphaltene dispersant composition is disclosed that comprises an alkylphenol copolymer having the following repeating units (A) and (B):

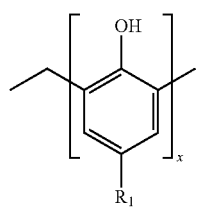

(A)

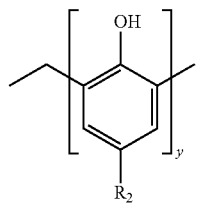

(B)

wherein,
x is an integer from 1 to 200;
y is an integer from 2 to 200;
$R_1$ is a straight or branched $C_1$-$C_{15}$ alkyl; and
$R_2$ is a straight or branched $C_2$-$C_{40}$ alkyl, wherein $R_2$ is different than $R_1$.

In accordance with another embodiment of the present invention, an asphaltene dispersant composition is disclosed that exhibits a percent asphaltene inhibition of about 80% or more as determined at a non-volatile residue percentage of 15%.

Other features and aspects of the present invention are set forth in greater detail below.

Definitions

It is to be understood that the terminology used herein is for the purpose of describing particular embodiments only and is not intended to limit the scope of the present invention.

"Alkyl" refers to monovalent saturated aliphatic hydrocarbyl groups and "$C_{x-y}$alkyl" refers to alkyl groups having from x to y carbon atoms. This term includes, by way of example, linear and branched hydrocarbyl groups, such as butyl ($CH_3(CH_2)_3$), octyl ($CH_3(CH_2)_7$), nonyl ($CH_3(CH_2)_8$), decyl ($CH_3(CH_2)_9$), undecyl ($CH_3(CH_2)_{10}$), dodecyl ($CH_3(CH_2)_{11}$), tridecyl ($CH_3(CH_2)_{12}$), tetradecyl ($CH_3(CH_2)_{13}$), pentadecyl ($CH_3(CH_2)_{14}$), hexadecyl ($CH_3(CH_2)_{15}$), heptadecyl ($CH_3(CH_2)_{16}$), octadecyl ($CH_3(CH_2)_{17}$), nonadecyl ($CH_3(CH_2)_{18}$), icosanyl ($CH_3(CH_2)_{19}$), henicosanyl ($CH_3(CH_2)_{20}$), docosanyl ($CH_3(CH_2)_{21}$), tricosanyl ($CH_3(CH_2)_{22}$), tetracosanyl ($CH_3(CH_2)_{23}$), pentacosanyl ($CH_3(CH_2)_{24}$), hexacosanyl ($CH_3(CH_2)_{25}$), heptacosanyl ($CH_3(CH_2)_{26}$), octacosanyl ($CH_3(CH_2)_{27}$), etc.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

DETAILED DESCRIPTION

Figure 1:
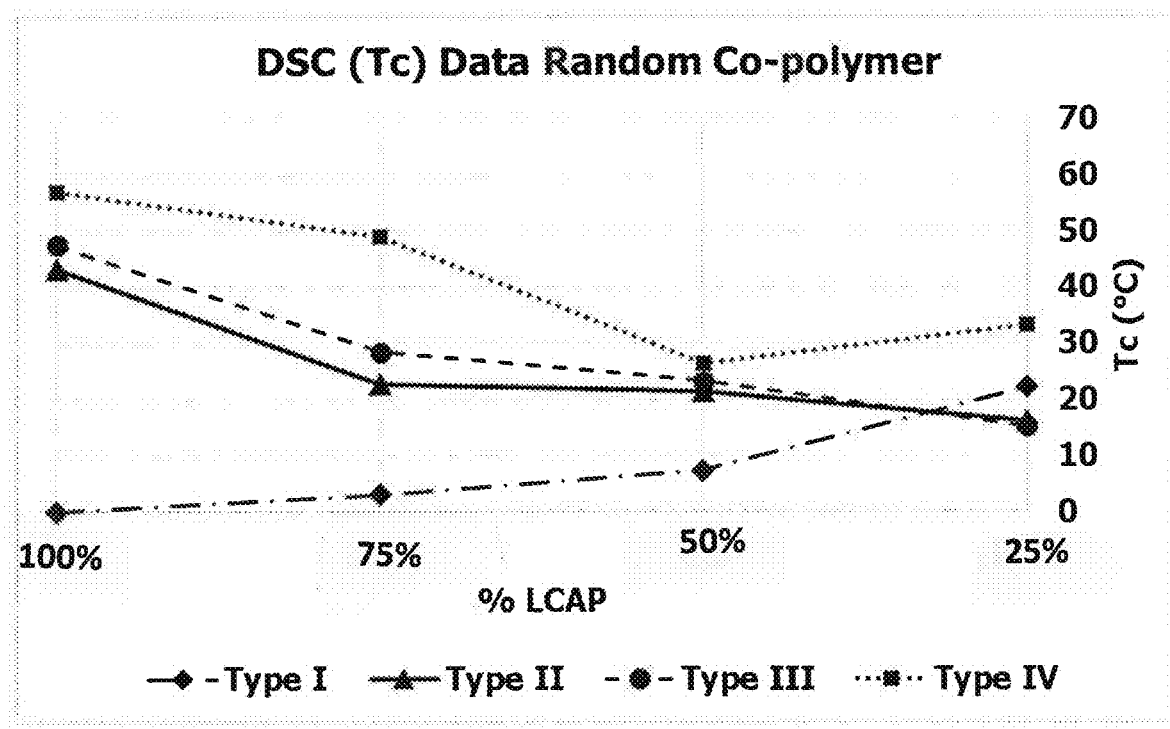
FIG. 1 is a graph showing the DSC data for the random copolymers of Examples 1-16.

It is to be understood by one of ordinary skill in the art that the present discussion is a description of exemplary embodiments only, and is not intended as limiting the broader aspects of the present invention.

Generally speaking, the present invention is directed to a composition that is capable of dispersing asphaltenes and/or inhibiting their formation in a petroleum source. For example, the asphaltene dispersancy parameter may be relatively low, such as about 250 or less, in some embodiments about 100 or less, in some embodiments about 50 or less, in some embodiments about 30 or less, and in some embodiments, from about 1 to about 15, as determined in substantial accordance with ASTM D7061-12 as described herein at a non-volatile residue percentage that may vary from 5% to 30% (e.g., 15%). Further, the percent asphaltene inhibition may also be about 50% or more, in some embodiments about 70% or more, in some embodiments about 80% or more, and in some embodiments, from about 90% to 100%, as determined in substantial accordance with ASTM D7061-12 as described herein at a non-volatile residue percentage that may vary from 5% to 30% (e.g., 15%). The composition of the present invention typically includes an alkylphenol copolymer having the following repeating units (A) and (B):

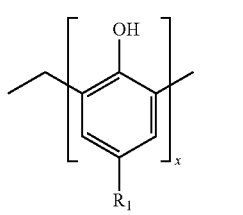

(A)

wherein, x is an integer from 1 to 200, in some embodiments from 1 to 100, in some embodiments from 1 to 50, and in some embodiments, from about 1 to about 25; and $R_1$ is a straight or branched $C_1$-$C_{15}$ alkyl, in some embodiments $C_2$-$C_{14}$ alkyl, in some embodiments $C_6$-$C_{14}$ alkyl, and in some embodiments, $C_8$-$C_{14}$ alkyl (e.g., $C_{12}$ alkyl); and

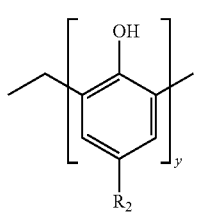

(B)

wherein, y is an integer from 2 to 200, in some embodiments from 3 to 100, in some embodiments from 4 to 50, and in some embodiments, from about 5 to about 25; and $R_2$ is a straight or branched $C_2$-$C_{40}$, in some embodiments $C_4$-$C_{40}$ alkyl, in some embodiments $C_8$-$C_{40}$, in some embodiments $C_{16}$-$C_{40}$ alkyl, in some embodiments $C_{18}$-$C_{36}$ alkyl, in some embodiments $C_{20}$-$C_{34}$ alkyl, and in some embodiments, $C_{24}$-$C_{32}$ alkyl, wherein $R_2$ is different than $R_1$. For example, the alkyl of $R_2$ typically contains 2 or more carbon atoms, in some embodiments 3 or more carbon atoms, in some embodiments 4 or more carbon atoms, and in some embodiments, 8 or more carbon atoms than the alkyl of $R_1$.

The present inventors have discovered that an appropriate balance between the content of the repeating units (A) and (B), as well as their respective molecular weights, may result in a copolymer having optimal properties for dispersing asphaltenes. Namely, the ratio of the moles of repeating unit (A) to the moles of repeating unit (B) is typically from about 0.2 to about 3, in some embodiments from about 0.5 to about 2, and in some embodiments, from about 0.8 to about 1.2. For example, the repeating unit (A) of the copolymer typically constitutes from about 20 mol. % to about 80 mol. %, in some embodiments from about 30 mol. % to about 70 mol. %, and in some embodiments, from about 40 mol. % to about 60 mol. % of the alkylphenol copolymer. Likewise, the repeating unit (B) typically constitutes from about 20 mol. % to about 80 mol. %, in some embodiments from about 30 mol. % to about 70 mol. %, and in some embodiments, from about 40 mol. % to about 60 mol. % of the alkylphenol copolymer. The number average molecular weight of the repeating unit (A) may range from about 300 to about 15,000 Daltons, in some embodiments from about 4,000 to about 12,000 Daltons, and in some embodiments, from about 4,000 to about 8,000 Daltons. The number average molecular weight of the repeating unit (B) may likewise range from about 300 to about 15,000 Daltons, in some embodiments from about 4,000 to about 12,000 Daltons, and in some embodiments, from about 4,000 to about 8,000 Daltons. The number average molecular weight of the entire copolymer may also range from about 4,000 to about 60,000 Daltons, in some embodiments from about 6,000 to about 30,000 Daltons, and in some embodiments, from about 8,000 to about 25,000 Daltons. Molecular weight may be determined using the gel permeation chromatography method described below. Of course, it should also be understood that other repeating units or constituents may also be present in the copolymer. For instance, the copolymer may contain another repeating unit (C) that is different than the repeating units (A) and/or (B). When employed, such repeating units typically constitute no more than about 20 mol. %, in some embodiments no more than about 10 mol. %, and in some embodiments, from about 0.1 to about 5 mol. % of the alkylphenol copolymer.

In addition, it should be understood that the alkylphenol copolymer as disclosed herein may also include ortho-substituted repeating units. For instance, while the repeating units employed in synthesizing the copolymer may primarily include para-substituted repeating units, in one embodiment, the copolymer may also include some ortho-substituted repeating units wherein the alkyl group is ortho to the hydroxyl group. In this regard, the molar ratio of the para-substituted repeating units to the ortho-substituted repeating units may be within a certain range. For instance, when the ortho-substituted repeating units are utilized, the molar ratio of the para-substituted repeating units to the ortho-substituted repeating units may be about 0.1 or more, such as about 0.2 or more, such as about 0.5 or more, such as about 1 or more, such as about 1.5 or more, such as about 2 or more, such as about 3 or more, such as about 4 or more, such as about 5 or more, such as about 9 or more, such as about 10 or more, such as about 15 or more, such as about 20 or more, such as about 25 or more, such as about 50 or more, such as about 75 or more, such as about 90 or more, such as about 95 or more, such as about 99 or more. When the ortho-substituted repeating units are utilized, the molar ratio of the para-substituted repeating units to the ortho-substituted repeating units may be about 100 or less, such as about 99 or less, such as about 98 or less, such as about 95 or less, such as about 90 or less, such as about 80 or less, such as about 70 or less, such as about 60 or less, such as about 50 or less, such as about 40 or less, such as about 30 or less, such as about 20 or less, such as about 10 or less, such as about 8 or less, such as about 6 or less, such as about 5 or less, such as about 4 or less, such as about 3 or less, such as about 2.5 or less, such as about 2 or less, such as about 1 or less.

The alkylphenol copolymer may also possess any desired configuration, such as block (diblock, triblock, tetrablock, etc.), random, alternating, graft, star, etc. Nevertheless, the present inventors have discovered that block copolymers are particularly effective for use in the present invention. Without intending to be limited by theory, it is believed that the presence of block oligomer segments can allow larger regions of the repeating units (A) and/or (B) to predominate throughout the polymer chain. This results in a more ordered structure, which can increase the degree to which the copolymer can disperse asphaltenes, such as determined in accordance with ASTM D7061-12 as described below. As a result of its highly ordered structure, the polymer typically has a relatively high crystalline melting temperature, such as about 30° C. or more, and in some embodiments, from about 40° C. to about 60° C. The polymer may also have a relatively low crystallization temperature, such as about 50° C. or less, and in some embodiments, from about 10° C. to about 30° C., as well as a low glass transition temperature, such as about 60° C., and in some embodiments, from about 10° C. to about 55° C. The melting temperature, crystallization temperature, and glass transition temperature may be determined using differential scanning calorimetry (DSC), as described in more detail below.

The alkylphenol copolymer may be formed using any known polymerization technique as is known in the art. In one embodiment, for example, the phenol monomers used to form the copolymer are reacted with a formaldehyde source in the presence of a catalyst. Suitable formaldehyde sources may include, for instance, formaldehyde (HCHO), paraform, trioxane, alkyaldehyde, etc. Likewise, suitable phenol monomers for forming the repeating units (A) may include, for instance, butylphenol, pentylphenol, hexylphenol, dodecylphenol, nonylphenol, octylphenol, etc., as well as mixtures thereof. Suitable phenol monomers for forming the repeating units (B) may likewise include butylphenol, nonylphenol, tetracosanylphenol, pentacosanylphenol, hexacosanylphenol, heptacosanylphenol, octacosanylphenol, etc., as well as mixtures thereof. A base or acid catalyst may be employed. Examples of suitable base catalysts include sodium hydroxide, barium hydroxide, potassium hydroxide, calcium hydroxide, organic amines, sodium carbonate, and combinations thereof. Examples of suitable acid catalysts include hydrochloric acid, sulfuric acid, phosphoric acid, sulfonic acid, sulfamido acids, haloacetic acids, and combinations thereof. In particular embodiments, a sulfonic acid catalyst (e.g., p-toluene sulfonic acid or dodecylbenzenesulfonic acid) is employed. The reaction typically occurs at an elevated temperature, such as a temperature of from about 50° C. to about 180° C., and in some embodiments, from about 80° C. to about 120° C.

The manner in which the reaction occurs can depend in part on the type of polymer that is being formed. For example, when forming a random alkylphenol copolymer, the phenol monomers may be reacted with a formaldehyde source within a single reaction vessel. In such embodiments, the ratio of the total number of moles of the formaldehyde source added to the reaction vessel to the total number of moles of the phenol monomers may range from about 0.5 to about 1, and in some embodiments, from about 0.8 to about 0.95. A similar technique may be employed when forming a block copolymer. In other cases, however, it may be desirable to initially form a prepolymer prior to completing the polymerization process. In this regard, the phenol monomer used to form the repeating units (A) may be reacted with formaldehyde in a first reaction vessel and the phenol monomer used to form the repeating units (B) may be reacted with the formaldehyde source in a second reaction vessel. In such embodiments, the ratio of the total number of moles of the formaldehyde source added to the first reaction vessel to the total number of moles of the phenol monomers used to form the repeating units (A) may range from about 0.5 to about 1, and in some embodiments, from about 0.6 to about 0.85, and the ratio of the total number of moles of the formaldehyde source added to the second reaction vessel to the total number of moles of the phenol monomers used to form the repeating units (B) may range from about 0.5 to about 1, and in some embodiments, from about 0.6 to about 0.85. Once the oligomers are formed, they may then be combined together in a reaction vessel and again reacted with a formaldehyde source to complete the polymerization and formation of a block copolymer. In such embodiments, the ratio of the total number of moles of the formaldehyde source added to the reaction vessel to the total number of moles of the oligomers may range from about 0.01 to about 0.5, and in some embodiments, from about 0.05 to about 0.2.

Regardless of the particular manner in which it is formed, the alkylphenol copolymer may be employed in the composition of the present invention to help inhibit the formation of asphaltenes in various oil formulations. The composition may be employed in the form of a concentrate that contains the alkylphenol copolymer as the primary ingredient or it may also be employed in the form of a dispersion or solution that contains one or more solvents in combination with the alkylphenol copolymer. Dilution may occur prior to use, or it may also occur in the field by an end user of the composition. When employed, suitable solvents may include organic solvents, such as aliphatic and/or aromatic hydrocarbons. Particularly suitable solvents include, for instance, petroleum-based solvents that include refined petroleum distillates or solvents. Refined petroleum distillates or solvents may include, for instance, aromatic compounds, such as benzene, toluene, xylene, light aromatic naphtha, heavy aromatic naphtha (HAN), kerosene, etc.; aliphatic compounds, such as pentane, hexane, heptane, octane, nonane, decane, undecane, dodecane, tridecane, tetradecane, pentadecane, hexadecane, etc.; as well as mixtures thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is a lower boiling material that is collected near the top portion of the distillation column. Medium naphtha is a higher boiling material that is collected from near the middle of the column. Finally, heavy naphtha is an even higher boiling material that is collected from near the bottom portion of the column. When solvents are employed, they typically constitute from about 30 wt. % to about 99 wt. %, in some embodiments from about 50 wt. % to about 95 wt. %, and in some embodiments, from about 60 wt. % to about 90 wt. % of the composition. Likewise, alkylphenol copolymer(s), such as described herein, may constitute from about 1 wt. % to about 70 wt. %, in some embodiments from about 5 wt. % to about 50 wt. %, and in some embodiments, from about 10 wt. % to about 40 wt. % of the composition.

In addition to an alkylphenol copolymer and solvent, the composition may also contain one or more additional ingredients as is known in the art, such as paraffin inhibitors, corrosion inhibitors, surfactants, neutralizers, stabilizers, plasticizers, biocides, preservatives, etc. Suitable corrosion inhibitors may include, for instance, sulfonates, imidazolines, amines, amides, esters, as well as salts and/or polymers thereof. Examples of amine corrosion inhibitors may include n-tetradecyl amine, n-hexadecylamine, lauryl amine, myristyl amine, palmityl amine, stearyl amine, and oleyl amine, etc. When employed, an additional ingredient may be combined with the alkylphenol copolymer at any point after it is formed. For instance, an additional ingredient may be combined with the copolymer after it is diluted with a solvent or it may be simultaneously added as the copolymer is being formed. Likewise, the additional ingredients may be added at a single point in time or combined with the copolymer in the field to form the composition, such as in response to a certain environmental condition. As an example, one or more additional ingredients may be combined with the alkylphenol copolymer just prior to transportation or storage, or even just prior to the addition of the copolymer to crude oil.

One example of a suitable additional ingredient is a surfactant, which may be employed in an amount of from about 0.1 wt. % to about 10 wt. %, and in some embodiments, from about 0.2 wt. % to about 1 wt. % of the composition. Suitable surfactants may include nonionic surfactants, amphoteric surfactants, and/or anionic surfactants. Examples of suitable nonionic surfactants may include, for instance, alkoxylated alcohols, such as copolymers of ethylene oxide and/or propylene oxide and/or butylene oxide and epoxylated, propoxylated, and epoxylated-propoxylated compounds formed from $C_6$-$C_{40}$ alkanols. Other nonionic surfactants may also be employed, such as alkylphenol alkoxylates (e.g., nonylphenol ethoxylate), block copolymers of ethylene, propylene and butylene oxides, alkyl polyglucosides, polyalkoxylated glycerides, sorbitan esters and polyalkoxylated sorbitan esters, and alkoyl polyethylene glycol esters and diesters. Examples of suitable amphoteric surfactants may include alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, betaines, sultaines, alkyl amphoacetates and amphodiacetates, alkyl amphopropionates and amphodipropionates, dodecylbenzene sulfonic acid, and alkyliminodipropionate. Likewise, examples of suitable anionic surfactants may include alkylbenzene sulfonates, alkyldiphenoxyether sulfonates and disulfonates, napthalene sulfonates, linear and branched alkyl sulfonates, fatty alcohol sulfates, fatty alcohol ether sulfates, linear and branched alpha olefin sulfonates.

Neutralizers may also be employed in the composition if desired. For example, unreacted formaldehyde and/or unused acid catalysts (e.g., dodecylbenzenesulfonic acid) can sometimes remain present within the composition. Unreacted formaldehyde can potentially act as a crosslinking agent that causes unwanted solidification at low temperatures, while unused acid catalysts potentially precipitate as seed crystals at low temperatures. Thus, a base compound may be added to neutralize these components, such as a compound that contains one or more amine moieties (e.g., alkyl amine). Suitable alkyl amines may include monoamines (e.g., methyl amine), diamines (e.g., ethylenediamine), triamines (e.g., diethylenetriamine), etc. When employed, the neutralizer may be added in an amount of from about 0.01 wt. % to about 1 wt. %, and in some embodiments, from about 0.05 wt. % to about 0.5 wt. % of the composition.

The asphaltene dispersant composition of the present invention may be used in a variety of applications. For example, the composition is typically added to a petroleum source, such as at a concentration of from about 10 to about 5,000 parts per million (ppm), in some embodiments from about 15 to about 1,800 ppm, and in some embodiments, from about 20 to about 1,500 ppm. The alkylphenol copolymer(s) may thus be present in the petroleum source at a concentration of from about 1 to about 1000 parts per million (ppm), in some embodiments from about 5 to about 300 ppm, and in some embodiments, from about 10 to about 250 ppm. The petroleum source may be a source of crude oil, another unrefined petroleum source, or a product derived therefrom, such as heating oil, fuel oil, bunker C oil, bitumen, etc.

As indicated above, one benefit of the composition of the present invention is that it can help disperse asphaltenes during storage and/or transportation of a petroleum source. For example, the composition may be readily poured or pumped from a storage container or vessel into contact with a petroleum source. The composition can be stored within a container for at least some period of time, removed from the container, and then applied to the petroleum source. The duration of storage may vary from about 1 day to five years, such as about 2 days to 1 year, or about 1 week to 6 months, or about 2 weeks to 4 months, or about 1 to 2 months. The method of applying the composition to the petroleum source is not particularly limited and can be conventionally added by using available equipment, such as pipes, mixers, pumps, tanks, injection ports, etc. In some embodiments, the composition is applied to one or more subterranean hydrocarbon recovery (oil well) locations, such as downhole or on the backside using capillary string, gas lift, slip stream or other methods, at the wellhead, or at any other point downstream of the reservoir. The composition may also be employed in combination with umbilical drilling equipment.

In addition to acting as an asphaltene dispersant, it should also be understood that the alkylphenol copolymer may also exhibit other beneficial properties. For instance, in certain embodiments, the copolymer may also function as a paraffin inhibitor. In such embodiments, when tested according to the Cold Finger method described herein, the composition can achieve a percent paraffinic wax deposition inhibition of about 50% or more, in some embodiments about 55% or more, and in some embodiments, from about 60% to about 90% for a given model oil fluid. Without intending to be limited by theory, the ability of the copolymer to function effectively at low temperatures is believed to be at least partially due to its ability to retain good solubility and flow properties at low temperatures. For example, the no-flow point of the copolymer may be relatively low, such as about −20° C. or less, in some embodiments about −30° C. or less, and in some embodiments, from about −30° C. to about −70° C., as determined in accordance with either ASTM D-7346-15 and at a non-volatile residue percentage that may vary from 5% to 30% (e.g., 15%). Likewise, the time to gel may be relatively high at low temperatures, such as about 500 seconds or more, in some embodiments about 600 seconds or more, and in some embodiments, from about 800 to about 14,400 seconds as determined at a temperature of −20° C. or −30° C. as determined according to the test method provided below. In addition to simply performing well at low temperatures, good properties can be maintained at a cold temperature site without risking gel formation over a broad range of temperatures.

The copolymer may also exhibit further beneficial properties indicative of improved performance at low temperatures. For instance, the copolymer may allow for a reduction in the cloud point temperature thereby indicating a reduction in the temperature at which point a sample becomes relatively cloudy and begins to solidify. In this regard, with the copolymer as disclosed herein, the cloud point depression (ΔCP) may be at least 0.5° C., such as at least 1° C., such as at least 1.5° C., such as at least 2° C., such as at least 2.5° C., such as at least 3° C., such as at least 3.5° C., such as at least 4° C. when determined in accordance with ASTM D-5773. The cloud point depression (ΔCP) may be 5° C. or less, such as 4.5° C. or less, such as 4° C. or less, such as 3.5° C. or less, such as 3° C. or less, such as 2.5° C. or less, such as 2° C. or less, such as 1° C. or less when determined in accordance with ASTM D-5773. Such depression may be realized at least at one copolymer dosage of 2000 ppm, 1000 ppm, 500 ppm, or 250 ppm.

Furthermore, the copolymer may also exhibit a reduced pour point thereby indicating a reduction in the temperature at which point the flow characteristics generally diminish. For instance, with the copolymer as disclosed herein, the pour point depression (ΔPP) may be at least 1° C., such as at least 3° C., such as at least 5° C., such as at least 8° C., such as at least 10° C., such as at least 20° C., such as at least 30° C., such as at least 50° C., such as at least 60° C., such as at least 65° C., such as at least 70° C. when determined in accordance with ASTM D-5949. The pour point depression (ΔPP) may be 100° C. or less, such as 90° C. or less, such as 80° C. or less, such as 75° C. or less, such as 70° C. or less, such as 60° C. or less, such as 50° C. or less when determined in accordance with ASTM D-5949. Such depression may be realized at least at one copolymer dosage of 2000 ppm, 1000 ppm, 500 ppm, or 250 ppm.

The present invention may be better understood with reference to the following examples.

Test Methods

Differential Scanning calorimetry (DSC): The following equipment was used for this test:
TA Instruments DSC Q2000 with RCS90 Cooling System
TA Instruments Advantage Software with TA Instrument Explorer for instrument control
TA Instruments Universal Analysis software for data analysis
TA Instruments Tzero DSC pans and lids (aluminum)
TA Instruments Tzero Press
Microbalance Initially, 8 to 11 mg of the sample (to the nearest 0.01 mg) was weighed into a Tzero aluminum pan so that the sample made good contact with the bottom of the pan. Using forceps, the pan lid was put into place and crimped to seal. The appropriate pre-weighed Tzero reference pan was also identified in the autosampler tray, and the autosampler was programed to load the reference pan along with the sample pan. The sample was then analyzed using the following conditions:
Purge Gas: Nitrogen
Purge Rate: 50 mL/min
Load Temperature: 40° C.
Temperature Profile: hold 3 minutes at 10° C., heat to 150° C. at a rate of 10° C/min, cool to 10° C. at a rate of 40° C./min, and hold 3 minutes at 10° C. (Cycle 1) and then heat again to 150° C. at a rate of 10° C./min (Cycle 2).

Gel Permeation Chromatography (GPC): The following equipment was used during this test:
Liquid Chromatograph: Agilent 1260 Series Liquid Chromatograph equipped with an Ultraviolet and/or a Refractive Index detector(s), auto-sampler and auto-injector
Cirrus GPC/SEC software v. 3.4.1, Chemstation OpenLab v. C.01.05
In-Line Pre-Column Filter Kit; SSI (Alltech): Filter housing, 35-0148, Replacement Filters, 2.0 µm, 05-0154
Chromatography Columns (Agilent):

| Pore Size(°A) | Dimensions |
| --- | --- |
| 500 | 300 mm × 7.5 mm × 5 µm |
| 1 × 10$^3$ | 300 mm × 7.5 mm × 5 µm |
| 1 × 10$^4$ | 300 mm × 7.5 mm × 5 µm |
| 1 × 10$^5$ | 300 mm × 7.5 mm × 5 µm |

2 mL glass vials with Teflon lined cap (Hewlett-Packard 5181-3400)
Scintillation Vials: 20 mL, Wheaton 12-986546
Pipets: disposable
50 mL amber dropping bottle The chromatograph operating parameters were also as follows:
Mobile Phase: 99/1 Tetrahydrofuran/Methanol
Flow: 1.2 mL/min
Injection Volume: 50 µL
UV Detector Wavelength: 280 nm (Samples), 254 nm (Standards)
Peak Threshold: System dependent-high enough to pick up the peaks but not so low that noise is detected
Peak Width: System dependent
Samples: Integration on 10 minutes, processing started before the sample baseline begins to rise (~10.1 minutes). The end processing time is the time of the baseline minimum just before phenol elutes. Phenol is injected in one of the standard sets and is used as a marker, even for samples that do not contain phenol.

For UV detection, 0.01 g (±0.01) of the sample was weighed into a 20 mL scintillation vial. The vial was filled with 4 mL of the 50 ppm sulfur in a tetrahydrofuran (THF) solution and dissolved. If the sample dissolved completely, it was transferred to a HPLC vial using a dropper pipet. If the sample appears cloudy, it was filtered through a 0.45 µM PTFE syringe filter before being added to the HPLC vial. For RI detection, 0.05 (±0.01) of the sample was weighed into a 20 mL scintillation vial. The vial was filled with 4mL of the mobile phase currently in use. If the sample dissolved completely, it was transferred to a HPLC vial using a dropper pipet. If the sample appeared cloudy, it was filtered through a 0.45 µM PTFE syringe filter before being added to the HPLC vial. Depending on the reliability of the pump, the standard solutions may be run as often as once every month. With the Cirrus software, each sample has a "Flow Rate Correction Factor", which compared the retention time of the sulfur from the sample run to the sulfur retention time from when the calibration table was created (for UV). If the times matched exactly, the factor was one. If the factor changed significantly, the flow was checked to ensure that the method flow was being obtained. If the flow was correct, the calibration standards were run to update the calibration table. Slight changes in the retention time of the sulfur may occur over time as the columns age, and sulfur shift in the UV detection indicates that recalibration should be performed for both detectors.

Asphaltene Dispersancy: The effectiveness of an asphaltene dispersant may be determined in substantial accordance with ASTM D7061-12. More particularly, depending on the grade of oil, the oil sample may need to be diluted with toluene before destabilizing with heptane. The asphaltenic fluid used in this test was prepared by dissolving a bitumen into a mixture of 70 vol. % aromatic 150 fluid (Solvesso 150) and 30 vol. % Exssol D60 at a non-volatile residue ("NVR") concentration of 10%, but was not heated to ensure homogeneity or further diluted with toluene as specified by ASTM D7061-12. Five (5) samples were initially prepared by adding 1.7 milligrams of a solution having a NVR concentration of 15% to an empty vial. The sample dispersant was then diluted to a total mass of 10 grams with crude oil using an analytical balance and combined with the NVR solution to form 25-ppm active dosed samples. The resulting sample solutions were then destabilized with 10-20 grams of n-heptane. One sample was left untreated to serve as a "blank", which was the internal standard for comparing the other treated crude oil samples. Once formed, all of the samples were re-mixed by inverting them 10 times before being loaded into a Turbiscan™ tower at a temperature set point of 30° C. (with a range capability of between 4° C. and 80° C.). The instrument transmits light into the sample (wavelength of 880 nm), where it is scattered by objects in suspension, such as droplets, solid particles, bubbles, etc. After scattering, the light emerges from the sample and is detected by the instruments detector system, which employs a mobile reading head having a NIR diode and two detectors (i.e., transmission detector and backscattering detector).

During the test, the Turbiscan™ tower measured the percent of light transmitted through the sample. The samples were scanned every two minutes over the period of 1 hour. The average percent transmission was recorded for each sample and graphed as a function of time and these values were calculated for the middle zone of the sample based on the instruments predefined zone settings. From this graph, the integrated area under the curve was calculated and recorded as the "asphaltene dispersancy parameter." The "percent asphaltene inhibition" relative to a blank was also determined by subtracting the area under the curve for a test sample from the area under the curve for an untreated blank, and then dividing this calculated difference by the area under the curve for the untreated blank. Generally speaking, those samples exhibiting smaller asphaltene dispersancy parameters (area under the curve) or a higher percent inhibition are considered better dispersants.

Cold Finger Evaluation of Model Oils: Cold finger experiments were run on a F5 Multi-place cold finger (F5 Technologie GmbH, Model .62) using four model oil types, i.e., Model Oil 1, Model Oil 3, Model Oil 4, and Model Oil 5. More particularly, the model oils contained a mixture of a known concentration of a certain type of refined waxes dissolved in a mixture of 70 vol. % aromatic 150 fluid (Solvesso 150) and 30 vol. % Exssol D60. The exact compositions are listed in Table 1.

TABLE 1

Model Oil Compositions

| Fluid | wt % Wax A | wt % Wax B | wt % Wax C | wt % Wax D | Total wt % waxes |
|---|---|---|---|---|---|
| Model Oil 1 | 5% WAKO 42-44 | 5% WAKO 66-68 | | | 10 |
| Model Oil 3 | 3% SASOL 4610 | 2% SASOL 4110 | 1% SASOL C80M | 0.1% SASOL H1 | 6.1 |
| Model Oil 4 | 5% SIGMA ALDRICH 53 | | | | 5 |
| Model Oil 5 | 5% SASOL 4610 | 5% SASOL 4110 | | | 10 |

To determine the experimental temperature conditions for both the bath temperature ($T_{oil}$) and the temperature for the finger ($T_f$), the wax appearance temperature (WAT or cloud point) of the untreated fluid was measured by differential scanning calorimetry (DSC) as described above. This onset temperature for wax precipitation was used to set $T_{oil}$, the bath temperature for heating the fluid in the cup, which was set between 0-8° C. above the WAT, and the finger temperature was set between 10 to 20° C. below $T_{oil}$. This differential in temperature between the bath and finger (target a ΔT=15° C. for each experiment) created a temperature gradient between the bulk fluid and the surface of the finger. The specific test conditions for all fluids are set forth below in Table 2.

TABLE 2

Cold Finger Conditions for Untreated Fluids

| Fluid | WAT (° C.) | $T_{oil}$ (° C.) | $T_f$ (° C.) | ΔT (° C.) | Avg. Blank deposit (g) | Time (hrs) |
|---|---|---|---|---|---|---|
| Model Oil 1 | 31.9 | 35 | 20 | 15 | 2.76 | 4 |
| Model Oil 3 | 36.6 | 36 | 21 | 15 | 0.91 | 4 |
| Model Oil 4 | 13.5 | 17 | 7 | 10 | 1.65 | 4 |
| Model Oil 5 | 27.8 | 31 | 16 | 15 | 1.81 | 4 |

To determine the final amount of material deposited onto the cold finger, the deposit was carefully removed from the cold finger cylinder and weighed. The experiments were run for a long enough period of time (e.g., greater than 4 hours) to deposit wax for an untreated sample such that the blank deposit was greater than 0.200 grams of wax. Samples were prepared by dosing the desired amount of test sample gravimetrically and mixing them with the required amount of preheated test fluids. The treated samples were conditioned in a temperature controlled oven set at 60-70° C. for a period of at least 4 hours before starting the cold finger experiment. In each experiment, an untreated blank was run concomitantly with the fluids treated with the experimental paraffin inhibitor. Based on the test procedure performed above, the paraffinic wax inhibition or percent reduction for a given test sample may then be determined by subtracting the weight of wax deposited by the test sample from the weight of wax deposited by the untreated blank, and then dividing this calculated difference by the weight of wax deposited by the untreated blank.

Rheological Evaluation: Rheology experiments were performed on a TA Discovery HR-1 stress controlled rheometer using a parallel plate geometry with a 40 mm diameter stainless steel upper plate and a Peltier-cooled bottom plate.

To minimize solvent loss during experiments, the solvent trap of the top plate was filled with the same solvent used to dissolve the sample and this trap was used in concert with a solvent trap cover that was placed over a Peltier stage. The Peltier solvent trap was equipped with gas inlet fittings and the geometry was swept with a slow stream of nitrogen to minimize water condensation during experiments performed below room temperature. Two methods were used to assess the flow properties of product formulations in aromatic 150 fluid solutions at a non-volatile residue ("NVR") concentration of 15%. The no-flow-point ("NFP") method was used to determine the temperature at which the sample no longer flowed when a controlled stress is applied to the sample while the temperature of the sample is decreased. The time-to-gel ("TTG") method was used to determine the time that it takes a sample to gel when held under static conditions at either −20° C. or −30° C. These test methods are described in more detail below.

No Flow Point: To perform this test, the Peltier stage was equilibrated to 40° C., the sample was loaded into a trim gap of 350 pm, and the sample was trimmed at a gap of 300 pm by drawing excess sample into a pipette. The sample was then conditioned by preheating to 80° C., holding for 600 seconds, and then initiating a preconditioning step in which the sample was sheared at a rate of 0.1 s$^{-1}$ for 150 seconds. The sample was then cooled to either 10° C. or 30° C. and then the oscillation temperature sweep was executed. Measurements were taken at 3° C. temperature steps with a stress of 0.4 Pa and an angular frequency of 0.25 rad/s. The reported value for the rheological no-flow-point was the temperature at which the oscillation displacement reached zero.

Time to Gel (TTG): To perform this test, the Peltier stage was equilibrated to 40° C., the sample was loaded into a trim gap of 350 μm and the sample was trimmed at a gap of 300 μm by drawing excess sample into a pipette. The sample was then conditioned by preheating to 80° C., holding for 600 seconds, and then initiating a preconditioning step in which the sample was sheared at a rate of 0.1 s$^{-1}$ for 150 seconds. Depending on the TTG method, the sample was then cooled to either −20° C. or −30° C., and then the oscillation time-to-gel was executed. Measurements were taken with a stress of 0.4 Pa and an angular frequency of 0.25 rad/s for a maximum duration of 14,400 seconds (4 hours). The reported value for the time-to-gel was the time for the loss modulus (G') and storage modulus (G") to crossover, with the exception for samples that pass the 4 hour window, which were reported as >4 hrs.

Cloud Point (CP) and Pour Point (PP): The following equipment was used for this test:

PhaseTechnology ASL-70Xi Autosampler Analyzer

The Phase Technology ASL-70Xi Autosampler Analyzer system is used to determine the cloud point (ASTM D5773) and pour point (ASTM D5949) of lube oils, fuels, and waxy paraffinic solutions. The cloud point and pour point were determined by following the ASTM methods developed and described for each test.

The cloud point and pour point tests are used to assess the ability of a sample to interact with the paraffinic components of a wax burdened fluid. The performance of any one sample is revealed by the measured depression of the both the cloud point and pour point temperature relative to a blank untreated sample. Furthermore, a dose-response over a range of concentrations can provide additional evidence of the magnitude of the interaction between the sample and the paraffin in solution. Samples were prepared by dosing the desired amount of test sample gravimetrically from 15% NVR stock solutions in A150 and mixing them with the required amount of preheated test fluids. The treated samples were conditioned in a temperature controlled oven set at 60-70° C. for a period of at least 4 hours before starting the cloud point and pour point tests. In each test, an untreated blank was run concomitantly with the test fluids treated with the experimental sample. All samples were compared against the average cloud point and pour point values for the untreated fluid. Based on the test procedure performed above, the cloud point depression (ΔCP) and pour point depression (ΔPP) for a given test sample may then be determined by subtracting the measured value of the test sample from the running average of the untreated blank.

Monomer Designations

For purposes of these Examples, the term "Type A" or "A-Type" monomer refers to para-dodecyl phenol ("PDDP") and the term "Type B" or "B-Type" monomer refers to a long-chain alkyl phenol ("LCAP"), i.e., $C_{16-18}$ alkyl phenol ("Type I"), $C_{24-28}$ alkyl phenol ("Type II"), $C_{26-28}$ alkyl phenol ("Type III"), and $C_{30+}$ alkyl phenol ("Type IV").

EXAMPLE 1

A polymer was formed from a Type I LCAP monomer resulting in a homopolymer of LCAP. Type I LCAP was loaded into a round bottom flask with 0.002 molar equivalents of dodecyl-benzyl-sulfonic acid and heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

EXAMPLE 2

A polymer was formed according to the procedure of Example 1, except that Example 2 used Type II LCAP and required 0.06 molar equivalents of additional 50% aq. formaldehyde to meet the target molecular weight.

EXAMPLE 3

A polymer was formed according to the procedure of Example 1, except that Example 3 used Type III LCAP and required 0.12 molar equivalents of additional 50% aq. formaldehyde to meet the target molecular weight.

EXAMPLE 4

A polymer was formed according to the procedure of Example 1, except that Example 4 used Type IV LCAP and required 0.20 molar equivalents of additional 50% aq. formaldehyde to meet the target molecular weight.

EXAMPLE 5

A polymer was formed from a combined mole ratio of 75:25 LCAP to Type A monomer resulting in a random copolymer of LCAP and Type A monomer. 0.75 molar equivalents of Type I LCAP was loaded into a round bottom flask with 0.25 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

EXAMPLE 6

A polymer was formed according to the procedure of Example 5, except that Example 6 used Type II LCAP and required 0.06 molar equivalents of additional 50% aq. formaldehyde to meet the target molecular weight.

EXAMPLE 7

A polymer was formed according to the procedure of Example 5, except that Example 7 used Type III LCAP and required 0.10 molar equivalents of additional 50% aq. formaldehyde to meet the target molecular weight.

EXAMPLE 8

A polymer was formed according to the procedure of Example 5, except that Example 8 used Type IV LCAP, required 0.17 molar equivalents of additional 50% aq. formaldehyde to meet the target molecular weight.

EXAMPLE 9

A polymer was formed from a combined mole ratio of 50:50 LCAP to Type A monomer resulting in a random copolymer of LCAP and Type A monomer. 0.5 molar equivalents of Type I LCAP was loaded into a round bottom flask with 0.5 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

EXAMPLE 10

A polymer was formed according to the procedure of Example 9, except that Example 10 used Type II LCAP and required 0.13 molar equivalents of additional 50% aq. formaldehyde to meet the target molecular weight.

EXAMPLE 11

A polymer was formed according to the procedure of Example 9, except that Example 11 used Type III LCAP and required 0.13 molar equivalents of additional 50% aq. formaldehyde to meet the target molecular weight.

EXAMPLE 12

A polymer was formed according to the procedure of Example 9, except that Example 12 used Type IV LCAP and required 0.27 molar equivalents of additional 50% aq. formaldehyde to meet the target molecular weight.

EXAMPLE 13

A polymer was formed from a combined mole ratio of 25:75 LCAP to Type A monomer resulting in a random copolymer of LCAP and Type A monomer. 0.25 molar equivalents of Type I LCAP was loaded into a round bottom flask with 0.75 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

EXAMPLE 14

A polymer was formed according to the procedure of Example 13, except that Example 14 used Type II LCAP and required 0.29 molar equivalents of additional 50% aq. formaldehyde to meet the target molecular weight.

EXAMPLE 15

A polymer was formed according to the procedure of Example 13, except that Example 15 used Type III LCAP and required 0.19 molar equivalents of additional 50% aq. formaldehyde to meet the target molecular weight.

EXAMPLE 16

A polymer was formed according to the procedure of Example 13, except that Example 16 used Type IV LCAP and required 0.16 molar equivalents of additional 50% aq. formaldehyde to meet the target molecular weight.

EXAMPLE 17

A polymer was formed from a combined mole ratio of 75:25 LCAP to Type A monomer oligomers resulting in a block co-polymer of LCAP and Type A monomer. A feedstock of Type A oligomer was made for the purposes of loading into future batches. Type A monomer was loaded into a round bottom flask with 0.002 molar equivalents of dodecyl-benzyl-sulfonic acid and then heated to a temperature from about 80° C. to about 120° C. 50% aqueous formaldehyde was loaded over 30 minutes, amounting to 0.75 molar equivalents of formaldehyde to Type A monomer, and the reaction was performed at a temperature from about 80° C. to about 120° C. under reflux. Using the GPC method to track molecular weight progression, the targeted molecular weight was achieved by post additions of 0.02 molar equivalents of 50% aq. formaldehyde. The reaction flask was then fitted with a Dean-Stark trap and the final reaction temperature was set to 140° C. to distill off all water. The Type A oligomer was set aside and another round bottom flask was loaded with 0.75 molar equivalents of Type II LCAP and 0.002 molar equivalents of dodecyl-benzyl-sulfonic acid and then heated to a temperature from about 80° C. to about 120° C. 0.75 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by post additions of 0.02 molar equivalents of 50% aq. formaldehyde. The final reaction temperature was then set to 140° C. to distill off all water. 0.25 molar equivalents of Type A oligomer was then loaded into the round bottom flask containing the 0.75 molar equivalents of Type II LCAP oligomer. Multiple additions of 50% aqueous formaldehyde were loaded until the targeted molecular weight was achieved. This example took 0.32 molar equivalents to reach the target molecular weight. The temperature was then set to 140° C. to distill off all water.

EXAMPLE 18

A polymer was formed according to the procedure of Example 17, except that Example 18 used Type III LCAP and required 0.22 molar equivalents of additional 50% aq. formaldehyde to meet the target molecular weight.

EXAMPLE 19

A polymer was formed according to the procedure of Example 17, except that Example 19 used Type IV LCAP and required 0.03 molar equivalents of additional 50% aq. formaldehyde to meet the target molecular weight.

EXAMPLE 20

A polymer was formed according to the procedure of Example 17, except that Example 20 used 50:50 Type II LCAP to Type A monomer, and required 0.10 molar equivalents of additional 50% aq. formaldehyde to meet the target molecular weight.

EXAMPLE 21

A polymer was formed according to the procedure of Example 17, except that Example 21 used 50:50 Type III LCAP to Type A monomer, and required 0.27 molar equivalents of additional 50% aq. formaldehyde to meet the target molecular weight.

EXAMPLE 22

A polymer was formed according to the procedure of Example 17, except that Example 22 used 50:50 Type IV LCAP to Type A monomer, and required 0.08 molar equivalents of additional 50% aq. formaldehyde to meet the target molecular weight.

EXAMPLE 23

A polymer was formed according to the procedure of Example 17, except that Example 23 used 25:75 Type II LCAP to Type A monomer, and required 0.13 molar equivalents of additional 50% aq. formaldehyde to meet the target molecular weight.

EXAMPLE 24

A polymer was formed according to the procedure of Example 17, except that Example 24 used 25:75 Type III LCAP to Type A monomer, and required 0.17 molar equivalents of additional 50% aq. formaldehyde to meet the target molecular weight.

EXAMPLE 25

A polymer was formed according to the procedure of Example 17, except that Example 25 used 25:75 Type IV LCAP to Type A monomer, and required 0.23 molar equivalents of additional 50% aq. formaldehyde to meet the target molecular weight.

Figure 2:
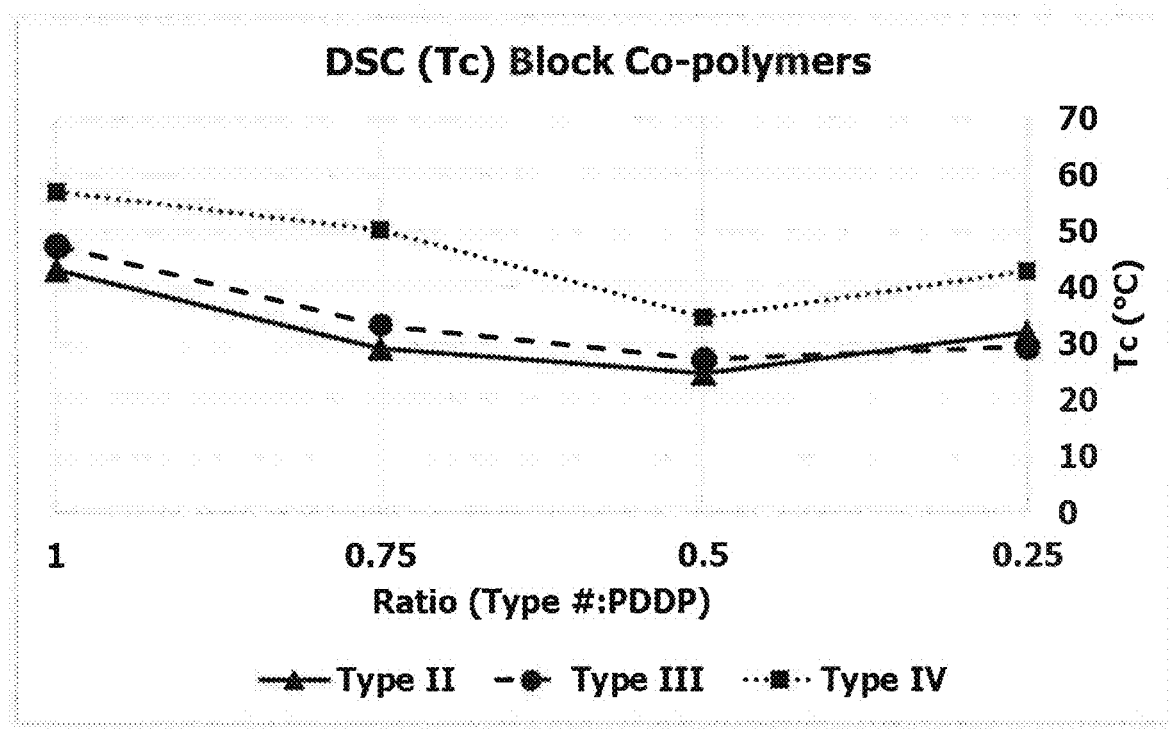
FIG. 2 is a graph showing the DSC data for the block copolymers of Examples 17-25.

A summary of the samples prepared in Examples 1-25 is provided below in Table 3 and also shown graphically in FIGS. 1-2.

TABLE 3

| Example | Type | Ratio | Polymer Type | DSC Tg [° C.] | MW (Da) |
|---|---|---|---|---|---|
| 1 | Type I | 100 | Random | 0 | 12117 |
| 2 | Type II | 100 | Random | 43.42 | 16637 |
| 3 | Type III | 100 | Random | 47.62 | 18602 |
| 4 | Type IV | 100 | Random | 57.18 | 18597 |
| 5 | Type I | 75 | Random | 3.08 | 14168 |
| 6 | Type II | 75 | Random | 22.91 | 14260 |
| 7 | Type III | 75 | Random | 28.64 | 15109 |
| 8 | Type IV | 75 | Random | 49.03 | 18671 |
| 9 | Type I | 50 | Random | 7.36 | 10749 |
| 10 | Type II | 50 | Random | 21.37 | 13838 |
| 11 | Type III | 50 | Random | 23.32 | 13822 |
| 12 | Type IV | 50 | Random | 26.56 | 15476 |
| 13 | Type I | 25 | Random | 22.35 | 10490 |
| 14 | Type II | 25 | Random | 16.09 | 11809 |
| 15 | Type III | 25 | Random | 15.25 | 11398 |
| 16 | Type IV | 25 | Random | 33.39 | 10440 |
| 17 | Type II | 75 | Block | 29.35 | 13624 |
| 18 | Type III | 75 | Block | 33.47 | 17653 |
| 19 | Type IV | 75 | Block | 50.54 | 16425 |
| 20 | Type II | 50 | Block | 34.59 | 11711 |
| 21 | Type III | 50 | Block | 27.35 | 14732 |
| 22 | Type IV | 50 | Block | 34.84 | 16708 |
| 23 | Type II | 25 | Block | 32.01 | 10587 |
| 24 | Type III | 25 | Block | 29.48 | 13613 |
| 25 | Type IV | 25 | Block | 43.01 | 11636 |

The DSC thermograms of the polymers listed in Table 3 are absent of any noticeable glass transition but are instead dominated by a rather large exothermic transition on the cooling cycle. The large exotherm in all of the samples is consistent with the crystallization of the long chain alkyl-sidechains of the Type B monomer. The observed reduction of crystallization is further consistent with the dilution that occurs going down the series of 75%, 50%, and 25% content for the long chain alkyl-sidechains of the Type B monomer by the addition of Type A monomer.

Once formed, the samples of Examples 2-4, 6-8, 10-12, and 14-25 were each diluted with a hydrocarbon solvent (aromatic 150 fluid) to form a composition containing 15 wt. % of the respective random or block copolymer. These compositions were then dosed at a concentration of 25 ppm and tested for asphaltene dispersancy as described above. The results are set forth below in Table 4.

TABLE 4

| Example | B-TYPE | % B-TYPE | P-TYPE | Area Under Curve | % Asphaltene Inhibition |
|---|---|---|---|---|---|
| 2 | TYPE II | 100% | random | 229.14 | 75.6% |
| 3 | TYPE III | 100% | random | 402.63 | 57.1% |
| 4 | TYPE IV | 100% | random | 917.06 | 2.3% |
| BLANK | | | | 938.42 | — |

TABLE 4-continued

| Example | B-TYPE | % B-TYPE | P-TYPE | Area Under Curve | % Asphaltene Inhibition |
|---|---|---|---|---|---|
| 6 | TYPE II | 75% | random | 136.11 | 86.5% |
| 7 | TYPE III | 75% | random | 235.62 | 76.6% |
| 8 | TYPE IV | 75% | random | 245.94 | 75.6% |
| BLANK | | | | 1009.00 | — |
| 10 | TYPE II | 50% | random | 7.26 | 99.2% |
| 11 | TYPE III | 50% | random | 39.60 | 95.9% |
| 12 | TYPE IV | 50% | random | 31.72 | 96.7% |
| BLANK | | | | 961.65 | — |
| 14 | TYPE II | 25% | random | 4.12 | 99.6% |
| 15 | TYPE III | 25% | random | 3.89 | 99.6% |
| 16 | TYPE IV | 25% | random | 2.93 | 99.7% |
| BLANK | | | | 1038.09 | — |
| 17 | TYPE II | 75% | block | 80.68 | 90.4% |
| 18 | TYPE III | 75% | block | 111.63 | 86.7% |
| 19 | TYPE IV | 75% | block | 146.83 | 82.5% |
| BLANK | | | | 837.96 | — |
| 20 | TYPE II | 50% | block | 7.55 | 99.2% |
| 21 | TYPE III | 50% | block | 6.80 | 99.2% |
| 22 | TYPE IV | 50% | block | 10.26 | 98.9% |
| BLANK | | | | 904.06 | — |
| 23 | TYPE II | 25% | block | 9.49 | 99.1% |
| 24 | TYPE III | 25% | block | 9.65 | 99.1% |
| 25 | TYPE IV | 25% | block | 8.54 | 99.2% |
| BLANK | | | | 1092.88 | — |

The samples of Examples 1-25 were also diluted with a hydrocarbon solvent (aromatic 150 fluid) to form a composition containing about 15 wt. % of the respective random or block copolymer, and then dosed at a concentration of 1,000 ppm into each of the fluids listed in Table 2. The Cold Finger paraffin inhibition was tested as set forth herein. In an effort to normalize the performance, a scoring system was also employed wherein any one additive is assigned three (3) points for reducing the wax deposit by at least 40% otherwise the additive is assigned one (1) point for failing to meet the 40% wax reduction metric. The results are set forth below in Tables 5-8.

TABLE 5

Cold Finger - MO1 Fluid

| Example | B-TYPE | % B-TYPE | POLYMER-TYPE | % reduction | Dose ppm | Score |
|---|---|---|---|---|---|---|
| 1 | TYPE I | 100% | random | 12% | 1000 | 1 |
| 2 | TYPE II | 100% | random | 69% | 1000 | 3 |
| 3 | TYPE III | 100% | random | 81% | 1000 | 3 |
| 4 | TYPE IV | 100% | random | 55% | 1000 | 3 |
| 5 | TYPE I | 75% | random | 1% | 1000 | 1 |
| 6 | TYPE II | 75% | random | 30% | 1000 | 1 |
| 7 | TYPE III | 75% | random | 95% | 1000 | 3 |
| 8 | TYPE IV | 75% | random | 54% | 1000 | 3 |
| 9 | TYPE I | 50% | random | 21% | 1000 | 1 |
| 10 | TYPE II | 50% | random | 3% | 1000 | 1 |
| 11 | TYPE III | 50% | random | 26% | 1000 | 1 |
| 12 | TYPE IV | 50% | random | 49% | 1000 | 3 |
| 13 | TYPE I | 25% | random | 22% | 1000 | 1 |
| 14 | TYPE II | 25% | random | 8% | 1000 | 1 |
| 15 | TYPE III | 25% | random | 23% | 1000 | 1 |
| 16 | TYPE IV | 25% | random | 23% | 1000 | 1 |
| 17 | TYPE II | 75% | block | 79% | 1000 | 3 |
| 18 | TYPE III | 75% | block | 75% | 1000 | 3 |
| 19 | TYPE IV | 75% | block | 80% | 1000 | 3 |
| 20 | TYPE II | 50% | block | 36% | 1000 | 1 |
| 20 | TYPE II | 50% | block | 66% | 1000 | 3 |
| 20 | TYPE II | 50% | block | 60% | 1000 | 3 |
| 20 | TYPE II | 50% | block | 50% | 1000 | 3 |
| 21 | TYPE III | 50% | block | 54% | 1000 | 3 |
| 22 | TYPE IV | 50% | block | 84% | 1000 | 3 |
| 23 | TYPE II | 25% | block | 73% | 1000 | 3 |
| 24 | TYPE III | 25% | block | 55% | 1000 | 3 |
| 25 | TYPE IV | 25% | block | 77% | 1000 | 3 |

TABLE 6

Cold Finger - MO3 Fluid

| Example | B-TYPE | % B-TYPE | POLYMER-TYPE | % reduction | Dose ppm | Score |
|---|---|---|---|---|---|---|
| 1 | TYPE I | 100% | random | 23% | 1000 | 1 |
| 2 | TYPE II | 100% | random | 74% | 1000 | 3 |
| 3 | TYPE III | 100% | random | 86% | 1000 | 3 |
| 4 | TYPE IV | 100% | random | 79% | 1000 | 3 |
| 5 | TYPE I | 75% | random | 4% | 1000 | 1 |
| 6 | TYPE II | 75% | random | 68% | 1000 | 3 |
| 7 | TYPE III | 75% | random | 76% | 1000 | 3 |
| 8 | TYPE IV | 75% | random | 81% | 1000 | 3 |
| 9 | TYPE I | 50% | random | 2% | 1000 | 1 |
| 10 | TYPE II | 50% | random | 37% | 1000 | 1 |
| 11 | TYPE III | 50% | random | 29% | 1000 | 1 |
| 12 | TYPE IV | 50% | random | 76% | 1000 | 3 |
| 13 | TYPE I | 25% | random | 4% | 1000 | 1 |
| 14 | TYPE II | 25% | random | 8% | 1000 | 1 |
| 15 | TYPE III | 25% | random | 16% | 1000 | 1 |
| 16 | TYPE IV | 25% | random | 56% | 1000 | 3 |
| 17 | TYPE II | 75% | block | 73% | 1000 | 3 |
| 18 | TYPE III | 75% | block | 69% | 1000 | 3 |
| 19 | TYPE IV | 75% | block | 81% | 1000 | 3 |
| 20 | TYPE II | 50% | block | 66% | 1000 | 3 |
| 21 | TYPE III | 50% | block | 55% | 1000 | 3 |
| 22 | TYPE IV | 50% | block | 76% | 1000 | 3 |
| 23 | TYPE II | 25% | block | 52% | 1000 | 3 |
| 24 | TYPE III | 25% | block | 52% | 1000 | 3 |
| 25 | TYPE IV | 25% | block | 79% | 1000 | 3 |

TABLE 7

Cold Finger - MO4 Fluid

| Example | B-TYPE | % B-TYPE | POLYMER-TYPE | % reduction | Dose ppm | Score |
|---|---|---|---|---|---|---|
| 1 | TYPE I | 100% | random | 6% | 1000 | 1 |
| 2 | TYPE II | 100% | random | 76% | 1000 | 3 |
| 3 | TYPE III | 100% | random | 69% | 1000 | 3 |
| 4 | TYPE IV | 100% | random | 14% | 1000 | 1 |
| 5 | TYPE I | 75% | random | −1% | 1000 | 1 |
| 6 | TYPE II | 75% | random | 67% | 1000 | 3 |
| 7 | TYPE III | 75% | random | 64% | 1000 | 3 |
| 8 | TYPE IV | 75% | random | 16% | 1000 | 1 |
| 9 | TYPE I | 50% | random | 10% | 1000 | 1 |
| 10 | TYPE II | 50% | random | 57% | 1000 | 3 |
| 11 | TYPE III | 50% | random | 58% | 1000 | 3 |
| 12 | TYPE IV | 50% | random | 36% | 1000 | 1 |
| 13 | TYPE I | 25% | random | −1% | 1000 | 1 |
| 14 | TYPE II | 25% | random | 27% | 1000 | 1 |
| 15 | TYPE III | 25% | random | 22% | 1000 | 1 |
| 16 | TYPE IV | 25% | random | 4% | 1000 | 1 |
| 17 | TYPE II | 75% | block | 70% | 1000 | 3 |
| 18 | TYPE III | 75% | block | 71% | 1000 | 3 |
| 19 | TYPE IV | 75% | block | 18% | 1000 | 1 |
| 20 | TYPE II | 50% | block | 50% | 1000 | 3 |
| 21 | TYPE III | 50% | block | 60% | 1000 | 3 |
| 22 | TYPE IV | 50% | block | 37% | 1000 | 1 |
| 23 | TYPE II | 25% | block | 17% | 1000 | 1 |
| 24 | TYPE III | 25% | block | 48% | 1000 | 3 |
| 25 | TYPE IV | 25% | block | 33% | 1000 | 1 |

TABLE 8

Cold Finger - MO5 Fluid

| Example | B-TYPE | % B-TYPE | POLYMER-TYPE | % reduction | Dose ppm | Score |
|---|---|---|---|---|---|---|
| 1 | TYPE I | 100% | random | 10% | 1000 | 1 |
| 2 | TYPE II | 100% | random | 57% | 1000 | 3 |
| 3 | TYPE III | 100% | random | 70% | 1000 | 3 |
| 4 | TYPE IV | 100% | random | 65% | 1000 | 3 |
| 5 | TYPE I | 75% | random | 18% | 1000 | 1 |
| 6 | TYPE II | 75% | random | 41% | 1000 | 3 |
| 7 | TYPE III | 75% | random | 61% | 1000 | 3 |
| 8 | TYPE IV | 75% | random | 67% | 1000 | 3 |
| 9 | TYPE I | 50% | random | 15% | 1000 | 1 |
| 10 | TYPE II | 50% | random | 24% | 1000 | 1 |
| 11 | TYPE III | 50% | random | 31% | 1000 | 1 |
| 12 | TYPE IV | 50% | random | 62% | 1000 | 3 |
| 13 | TYPE I | 25% | random | −7% | 1000 | 1 |
| 14 | TYPE II | 25% | random | −14% | 1000 | 1 |
| 15 | TYPE III | 25% | random | −139% | 1000 | 1 |
| 16 | TYPE IV | 25% | random | 4% | 1000 | 1 |
| 17 | TYPE II | 75% | block | 65% | 1000 | 3 |
| 18 | TYPE III | 75% | block | 70% | 1000 | 3 |
| 19 | TYPE IV | 75% | block | 53% | 1000 | 3 |
| 20 | TYPE II | 50% | block | 59% | 1000 | 3 |
| 21 | TYPE III | 50% | block | 55% | 1000 | 3 |
| 22 | TYPE IV | 50% | block | 61% | 1000 | 3 |
| 23 | TYPE II | 25% | block | 40% | 1000 | 3 |
| 24 | TYPE III | 25% | block | 43% | 1000 | 3 |
| 25 | TYPE IV | 25% | block | 46% | 1000 | 3 |

Figure 3:
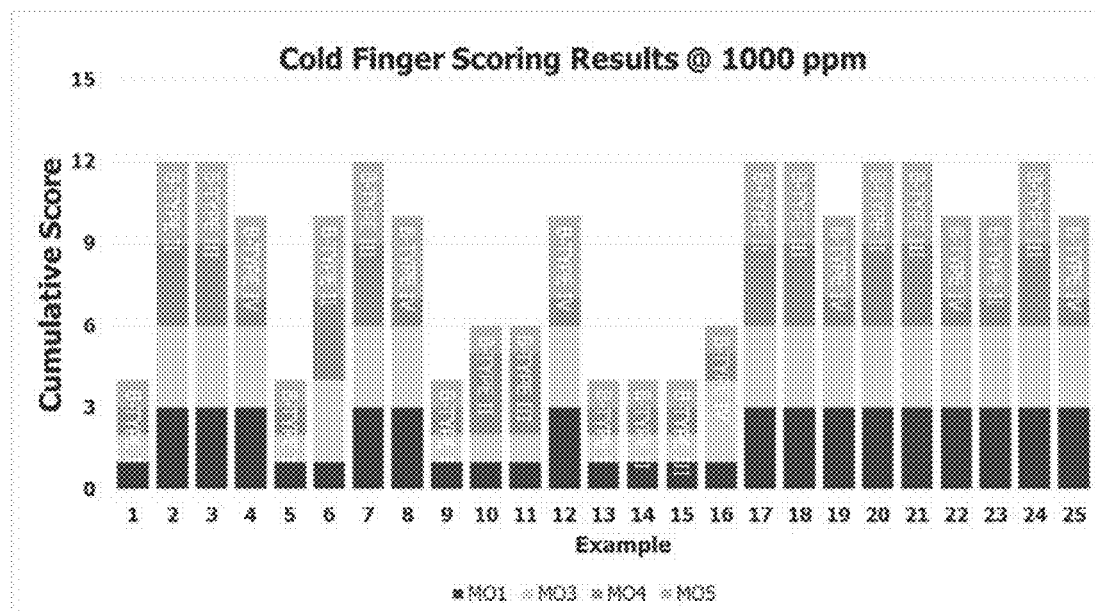
FIG. 3 is a graph showing the cumulative scoring results (at 1,000 ppm) of Cold Finger testing for the samples of Examples 1-25.
Figure 4:
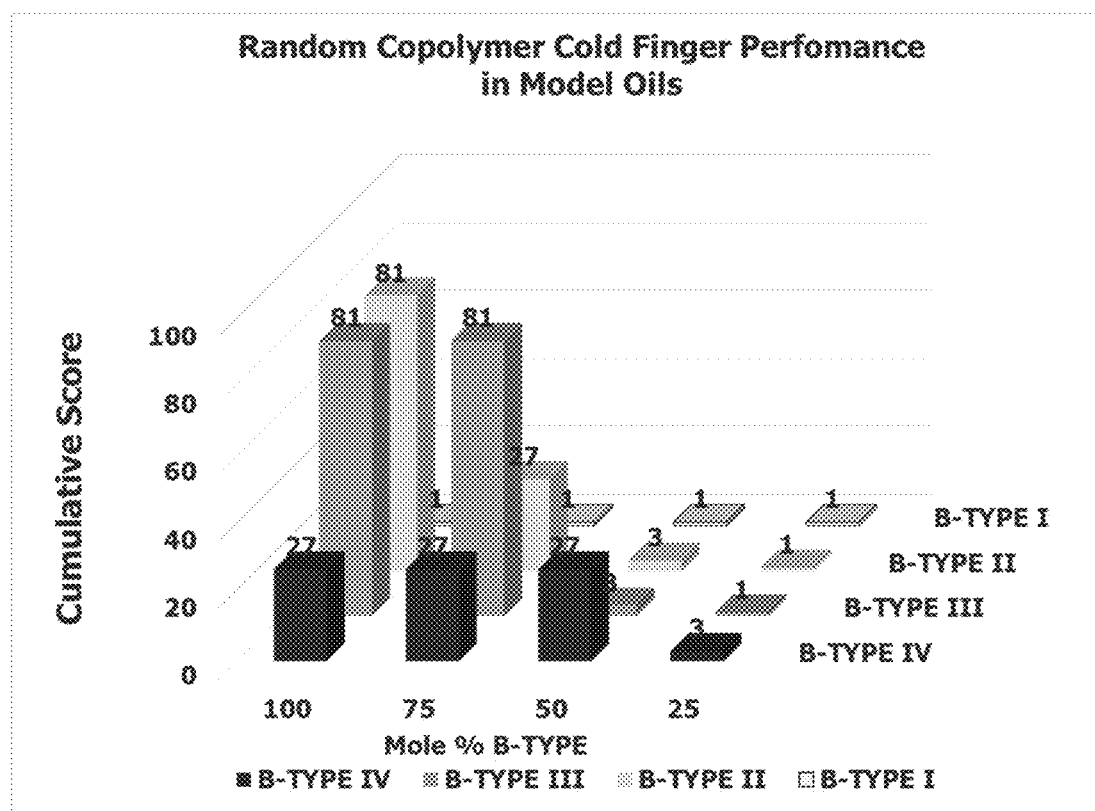
FIG. 4 is a graph showing the cumulative scoring results of Cold Finger testing for the random copolymer samples of Examples 1-16.
Figure 5:
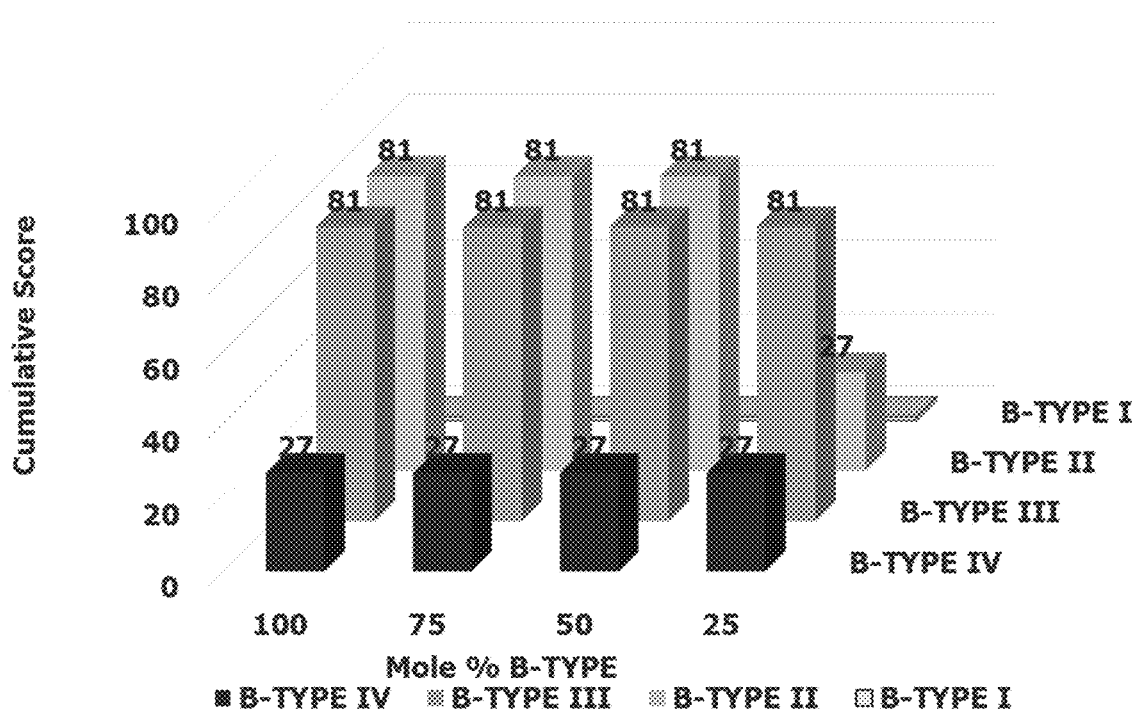
FIG. 5 is a graph showing the cumulative scoring results of Cold Finger testing for the block copolymer samples of Examples 17-25.

The underlying Cold Finger performance trends for the samples of Examples 1-25 copolymers are also shown graphically in FIGS. 3-5. As shown, the highest possible score was 81 followed by 27, 9, 3, and 1. For the random copolymers, the best performing additives were clustered in the region wherein they contain at least 75% Type B monomer (FIG. 4). For the block copolymers, there was a marked increase in performance for the entire range of polymers that contained 25% of the Type B monomer (FIG. 5). The same boost in performance was also observed for the block copolymers of 50% Type II and 50% Type III B monomers (FIG. 5).

No-flow point and time-to-gel testing was also performed for several of the samples using a 15% non-volatile residue ("NVR") percentage. The results are set forth below in Table 9.

TABLE 9

No-Flow Point and Time-To-Gel of 15% NVR Formulations

| Example | B-TYPE | POLYMER-TYPE | % B-TYPE | No-Flow Point$_{OSC}$ (° C.) | Time-to-Gel @ −20° C. | Time-to-Gel @ −30° C. |
|---|---|---|---|---|---|---|
| 2 | TYPE II | random | 100% | −14 | n.r. | n.r. |
| 3 | TYPE III | random | 100% | −2 | n.r. | n.r. |
| 4 | TYPE IV | random | 100% | 0 | n.r. | n.r. |
| 6 | TYPE II | random | 75% | −33 | 12272 | 285 |
| 7 | TYPE III | random | 75% | −20 | n.r. | n.r. |
| 8 | TYPE IV | random | 75% | −35 | 13000 | 0 |
| 10 | TYPE II | random | 50% | −38 | >4 hrs | 0 |
| 11 | TYPE III | random | 50% | −38 | >4 hrs | >4 hrs |
| 12 | TYPE IV | random | 50% | −38 | >4 hrs | >4 hrs |
| 17 | TYPE II | block | 75% | −26 | 7328 | 0 |
| 18 | TYPE III | block | 75% | −11 | n.r. | n.r. |
| 19 | TYPE IV | block | 75% | −38 | >4 hrs | 0 |
| 20 | TYPE II | block | 50% | −38 | >4 hrs | >4 hrs |
| 21 | TYPE III | block | 50% | −33 | >4 hrs | >4 hrs |
| 22 | TYPE IV | block | 50% | −38 | >4 hrs | >4 hrs |
| 23 | TYPE II | block | 25% | −38 | >4 hrs | >4 hrs |
| 24 | TYPE III | block | 25% | −38 | >4 hrs | >4 hrs |
| 25 | TYPE IV | block | 25% | −38 | >4 hrs | >4 hrs |

Two random copolymers (50% B-TYPE II and B-TYPE III) had no-flow point values of −38° C. and also passed the 4 hour time-to-gel evaluation at −20° C. and −30° C. Further, six out of the nine block copolymers were unexpectedly observed to have no-flow point values of −38° C. and also passed the 4 hour time-to-gel evaluation at −20° C. and −30° C.

The cloud point and pour point testing was also performed for Samples 17-19. In the analysis, the blank sample oil exhibited an average cloud point of 30.8° C. and an average pour point of 30° C. The results are set forth below in Table 10.

TABLE 10

Cloud Point and Pour Point

| Example | Dose (PPM) | B-TYPE | P-TYPE | % B-TYPE | CP (° C.) | PP (° C.) | ΔCP (° C.) | ΔPP (° C.) |
|---|---|---|---|---|---|---|---|---|
| 17 | 2000 | TYPE II | blocky | 75% | 28.0 | −39 | 2.8 | 69 |
| 17 | 1000 | TYPE II | blocky | 75% | 28.4 | −6 | 2.4 | 36 |
| 17 | 500 | TYPE II | blocky | 75% | 29.0 | 3 | 1.9 | 27 |
| 17 | 250 | TYPE II | blocky | 75% | 29.3 | 21 | 1.5 | 9 |
| 18 | 2000 | TYPE III | blocky | 75% | 28.3 | −24 | 2.5 | 54 |
| 18 | 1000 | TYPE III | blocky | 75% | 28.6 | −3 | 2.3 | 33 |
| 18 | 500 | TYPE III | blocky | 75% | 29.0 | 6 | 1.8 | 24 |
| 18 | 250 | TYPE III | blocky | 75% | 29.3 | 18 | 1.5 | 12 |
| 19 | 2000 | TYPE IV | blocky | 75% | 26.3 | 6 | 4.5 | 24 |
| 19 | 1000 | TYPE IV | blocky | 75% | 27.1 | 6 | 3.7 | 24 |
| 19 | 500 | TYPE IV | blocky | 75% | 27.9 | 15 | 2.9 | 15 |
| 19 | 250 | TYPE IV | blocky | 75% | 28.4 | 21 | 2.4 | 9 |

Each sample demonstrated a reduction in the cloud point and pour point. In particular, Examples 17 and 18 at a 2000 ppm dose exhibited a pour point of −39° C. and −24° C., respectively.

PROPHETIC EXAMPLE 1

A block copolymer may be formed as described in Example 17, except that $C_9$ alkyl phenol can be used instead of Type II LCAP.

PROPHETIC EXAMPLE 2

A block copolymer may be formed as described in Example 17, except that $C_4$ alkyl phenol can be used instead of Type II LCAP.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An asphaltene dispersant composition comprising an alkylphenol copolymer having the following repeating units (A) and (B):

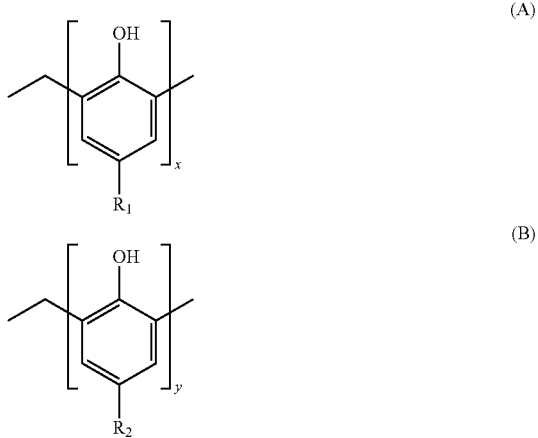

wherein,
x is an integer from 1 to 200;
y is an integer from 2 to 200;
$R_1$ is a straight or branched $C_1$-$C_{15}$ alkyl; and
$R_2$ is a straight or branched $C_2$-$C_{40}$ alkyl, wherein $R_2$ is different than $R_1$.

2. The asphaltene dispersant composition of claim 1, wherein $R_1$ is $C_8$-$C_{14}$ alkyl.

3. The asphaltene dispersant composition of claim 1, wherein $R_2$ is $C_{16}$-$C_{40}$ alkyl.

4. The asphaltene dispersant composition of claim 3, wherein $R_2$ is $C_{24}$-$C_{32}$ alkyl.

5. The asphaltene dispersant composition of claim 1, wherein the alkyl of $R_2$ contains 3 or more carbon atoms than the alkyl of $R_1$.

6. The asphaltene dispersant composition of claim 1, wherein x and y are independently from 5 to 25.

7. The asphaltene dispersant composition of claim 1, where the ratio of the moles of repeating unit (A) to the moles of repeating unit (B) is from about 0.2 to about 3.

8. The asphaltene dispersant composition of claim 1, wherein the number average molecular weight of the alkylphenol copolymer is from about 4,000 to about 60,000 Daltons.

9. The asphaltene dispersant composition of claim 1, wherein the alkylphenol copolymer is a random copolymer.

10. The asphaltene dispersant composition of claim 1, wherein the alkylphenol copolymer is a block copolymer.

11. The asphaltene dispersant composition of claim 10, wherein the block copolymer is formed by a process that comprises:
reacting a phenol monomer used to form the repeating units (A) with a formaldehyde source in a first reaction vessel to form a first oligomer;
reacting a phenol monomer used to form the repeating units (B) with a formaldehyde source in a second reaction vessel to form a second oligomer; and
thereafter, reacting the first oligomer and the second oligomer with a formaldehyde source to form the block copolymer.

12. The asphaltene dispersant composition of claim 11, wherein the ratio of the total number of moles of the formaldehyde source added to the first reaction vessel to the total number of moles of the phenol monomers used to form the repeating units (A) is from about 0.5 to about 1.

13. The asphaltene dispersant composition of claim 11, wherein the ratio of the total number of moles of the formaldehyde source added to the second reaction vessel to the total number of moles of the phenol monomers used to form the repeating units (B) is from about 0.5 to about 1.

14. The asphaltene dispersant composition of claim 11, wherein the phenol monomer used to form the repeating units (A) includes dodecylphenol.

15. The asphaltene dispersant composition of claim 11, wherein the phenol monomer used to form the repeating units (B) includes butylphenol, nonylphenol, tetracosanylphenol, pentacosanylphenol, hexacosanylphenol, heptacosanylphenol, octacosanylphenol, or a combination thereof.

16. The asphaltene dispersant composition of claim 1, wherein the composition exhibits an asphaltene dispersancy parameter of about 500 or less as determined at a non-volatile residue percentage of 15%.

17. The asphaltene dispersant composition of claim 1, wherein the composition exhibits a percent asphaltene inhibition of about 50% or more as determined at a non-volatile residue percentage of 15%.

* * * * *